(12) United States Patent
Phelps et al.

(10) Patent No.: US 6,891,311 B2
(45) Date of Patent: May 10, 2005

(54) ULTRASOUND TRANSMIT PULSER WITH RECEIVE INTERCONNECTION AND METHOD OF USE

(75) Inventors: Robert Phelps, Sammamish, WA (US); David A. Petersen, Fall City, WA (US)

(73) Assignee: Siemens Medical Solutions USA, INC, Malvern, PA (US)

(*) Notice: Subject to any disclaimer, the term of this patent is extended or adjusted under 35 U.S.C. 154(b) by 34 days.

(21) Appl. No.: 10/247,379

(22) Filed: Sep. 18, 2002

(65) Prior Publication Data

US 2004/0000841 A1 Jan. 1, 2004

Related U.S. Application Data

(63) Continuation-in-part of application No. 10/185,404, filed on Jun. 27, 2002, now Pat. No. 6,806,623, and a continuation-in-part of application No. 10/184,461, filed on Jun. 27, 2002, and a continuation-in-part of application No. 10/184,785, filed on Jun. 27, 2002.

(51) Int. Cl.[7] .............................................. H01L 41/08
(52) U.S. Cl. ........................ 310/317; 310/319; 310/334
(58) Field of Search ........................... 310/316.01, 317, 310/319, 334–337; 318/116–118

(56) References Cited

U.S. PATENT DOCUMENTS

| | | | | |
|---|---|---|---|---|
| 3,166,731 A | * | 1/1965 | Joy ............................. | 73/596 |
| 4,202,215 A | * | 5/1980 | Meyer ......................... | 73/599 |
| 4,550,606 A | * | 11/1985 | Drost .......................... | 73/626 |
| 4,629,927 A | * | 12/1986 | Samodovitz ................ | 310/334 |
| 4,644,214 A | * | 2/1987 | Takamizawa et al. ....... | 310/334 |
| 4,841,492 A | * | 6/1989 | Russell ....................... | 367/105 |
| 5,276,657 A | * | 1/1994 | Newnham et al. .......... | 367/157 |
| 5,327,895 A | * | 7/1994 | Hashimoto et al. ......... | 600/459 |
| 5,592,730 A | | 1/1997 | Greenstein et al. | |
| 5,622,177 A | | 4/1997 | Breimesser et al. | |
| 5,732,706 A | | 3/1998 | White et al. | |
| 5,764,596 A | | 6/1998 | Hanafy et al. | |
| 5,894,646 A | | 4/1999 | Hanafy et al. | |
| 5,957,851 A | | 9/1999 | Hossack | |
| 6,014,473 A | | 1/2000 | Hossack et al. | |
| 6,043,589 A | | 3/2000 | Hanafy | |
| 6,043,590 A | | 3/2000 | Gilmore | |
| 6,050,945 A | | 4/2000 | Peterson et al. | |
| 6,083,164 A | | 7/2000 | Oppelt et al. | |
| 6,104,126 A | | 8/2000 | Gilmore | |
| 6,106,472 A | * | 8/2000 | Chiang et al. ............... | 600/447 |
| 6,236,142 B1 | * | 5/2001 | Durkee ........................ | 310/319 |
| 6,375,618 B1 | * | 4/2002 | Chiao et al. ................. | 600/447 |
| 6,432,055 B1 | | 8/2002 | Carp et al. | |
| 6,558,331 B1 | * | 5/2003 | Davidsen et al. ............ | 600/459 |

OTHER PUBLICATIONS

"Real–Time Rectilinear Volumetric Imaging Using Receive Mod Multiplexing," by J.T. Yen and S.W. Smith at the Department of Biomedical Engineering, Duke University, Durham, NC; May 13, 2002.

* cited by examiner

Primary Examiner—Mark Budd (57) ABSTRACT

A transmit pulser includes an H-bridge of four transistors. First and second transistors of the H-bridge connect with a first electrode of a transducer element, and third and fourth transistors of the H-bridge connect with a second electrode of the transducer element. A differential receive amplifier connects with the first and third transistors. First and second diode clamps connect with the first and third transistors, respectively, and the inputs to the differential receive amplifier. The second and fourth transistors connect to a same power or voltage source, imposing a same voltage in either a forward or a reverse direction. By using matched transistor pairs (e.g. first and third matched pair and second and fourth matched pair), symmetrical transmit waveforms are generated. Symmetrical transmit waveforms allow for using phase inversion or phase differences between transmit waveforms for imaging, such as for harmonic imaging of tissue. The spectral content of symmetrical waveforms is narrower or includes less harmonic information.

22 Claims, 5 Drawing Sheets

ULTRASOUND TRANSMIT PULSER WITH RECEIVE INTERCONNECTION AND METHOD OF USE

RELATED APPLICATIONS

This application is a continuation-in-part of U.S. Pat. No. 6,806,623 (application Ser. No. 10/185,404), (application Ser. No. 10/184,461) and (application Ser. No. 10/184,785), all filed on Jun. 27, 2002, the disclosures of which are incorporated herein by reference.

BACKGROUND

The present invention relates to transmit pulsers for ultrasound imaging. In particular, transmit pulsers with interconnections to receive circuits are provided.

Ultrasound imaging for echocardiography applications requires transducers with high volume-per-second rates for scanning. For real-time imaging of moving structures, 20 or more, such as 35, two or three-dimensional representations are generated each second. Large amounts of information are communicated from an ultrasound probe to an ultrasound system base unit.

Various transducers and associated beamformers have been provided for three-dimensional ultrasound imaging. Currently, mostly mechanical transducers are used. However, the associated imaging is not provided in real time and typically requires ECG gating. Two-dimensional transducer arrays for faster electronic/electronic steering and volume acquisition also have been provided. For example, sparse two-dimensional arrays or fully sampled two-dimensional arrays have been used. Sparse arrays provide poor contrast resolution.

Fully sampled two-dimensional arrays use expensive additional beamforming hardware. Two-dimensional arrays repetitively generate transmit beams and responsive receive beams. The beams are electronically steered within the three-dimensional volume. Electronic steering requires a system channel for each of the elements used. Since the number of elements in a two-dimensional array is high, the number of channels required is high. More channels require a greater number of cables. Providing beamforming or partial beamforming within the probe of the transducer array may reduce the number of cables required, but the required number of channels and hardware for sampling the two-dimensional array is still high. Furthermore, analog delays used for beamforming in the probe are expensive and large, and the beamformer in the probe may have limited programmability.

Transducer arrays include elements with a ground electrode and a signal electrode switchably connected to separate transmit and receive system channels. With beamforming capabilities built into the probe, high voltage transistors or diodes operating as switches to isolate the transmit channels from the receive channels are also included within the probe. These high voltage devices are not easily integrated with the beamforming circuitry, so require additional space.

In one system disclosed in U.S. Pat. No. 5,622,177, the number of system channels and cables is reduced by using time division multiplexing. Data from a plurality of elements is multiplexed onto one signal line. However, time division multiplexed data has different characteristics than conventional data representing the signal from a single transducer element. Receive circuitry designed for use with conventional data may improperly introduce noise or errors in time division multiplexed data.

BRIEF SUMMARY

By way of introduction, the preferred embodiments described below include ultrasound transmit pulsers with receive interconnection and associated methods of use. A first switch connects between the transducer element and a receive amplifier. A second switch connects between a transducer element and power source. Both switches are used to generate a transmit waveform. The second switch connected with the power source is opened and the first switch connected with the receive amplifier is then closed during receive operation. A diode clamp connected with the receive amplifier and the first switch clamp the voltage at the receive amplifier, acting as a virtual ground during high voltage transmit operation but allowing the much smaller amplitude receive signals to pass to the receive amplifier during low voltage receive operation.

In one aspect, an H-bridge of transistors includes four transistors. First and second transistors of the H-bridge connect with a first electrode of a transducer element, and third and fourth transistors of the H-bridge connect with a second electrode of the transducer element. A differential receive amplifier connects with the first and third transistors. First and second diode clamps connect with the first and third transistors, respectively, and the inputs to the differential receive amplifier. The second and fourth transistors connect to a same power or voltage source, imposing a same voltage in either a forward or a reverse direction. By using matched transistor pairs (e.g. first and third matched pair and second and fourth matched pair), symmetrical transmit waveforms are generated. Symmetrical transmit waveforms allow for using phase inversion or phase differences between transmit waveforms for imaging, such as for harmonic imaging of tissue. The spectral content of symmetrical waveforms contains less even harmonic information.

The present invention is defined by the following claims, and nothing in this section should be taken as a limitation on those claims. Further aspects and advantages of the invention are discussed below in conjunction with the preferred embodiments.

BRIEF DESCRIPTION OF SEVERAL VIEWS OF THE DRAWINGS

The components and figures are not necessarily to scale, emphasis instead being placed upon illustrating the principles of the invention. Moreover, in the figures, like reference numerals designate corresponding parts throughout the different views.

DETAILED DESCRIPTION OF THE PREFERRED EMBODIMENTS

Figure 12:
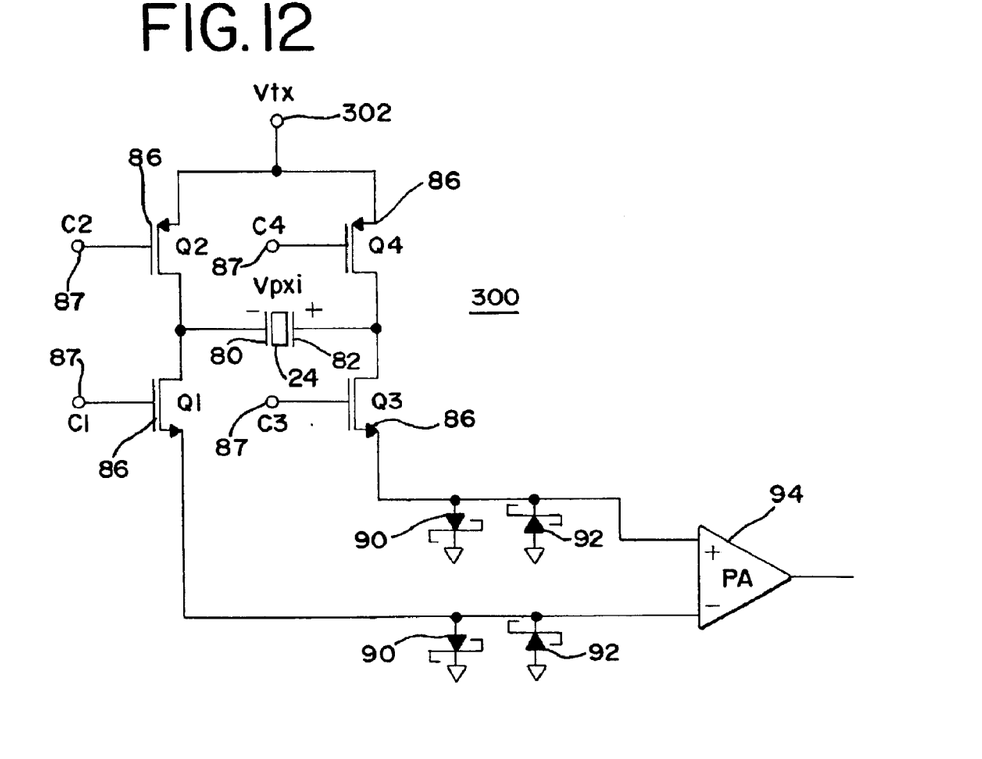
FIG. 12 is a circuit diagram of one embodiment of a transmit pulser with receive interconnection.

A transmit pulser with an interconnection to a receive preamplifier disclosed in FIG. 12 provides substantially symmetrical transmit waveforms. An H-bridge of transistors connects with a transducer element between a power source and a differential receive preamplifier. Diode clamps connect with inputs to the differential receive preamplifier. By using matched transistor pairs, symmetrical transmit waveforms are generated. The transmit pulser may be implemented in an application specific integrated circuit within a probe. By implementing the transmit pulser in the probe, a larger number of transducer elements may be used without requiring additional cables connected between the probe housing and a base imaging unit.

Figure 3:
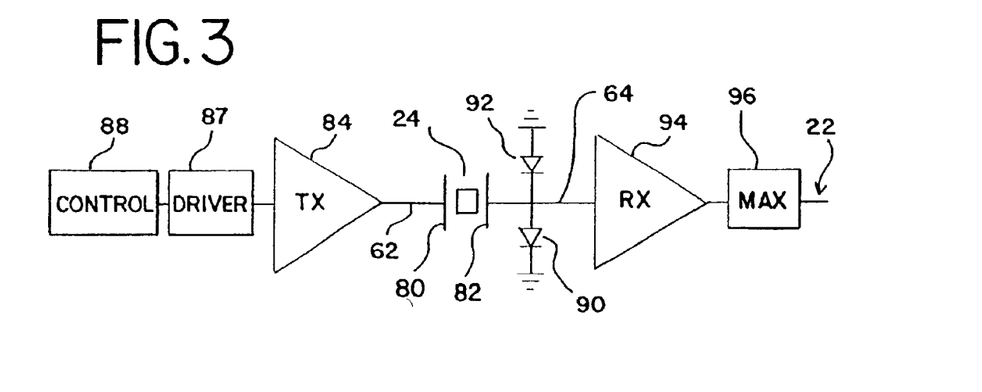
FIG. 3 is a block diagram of one embodiment of a transducer with isolated transmit and receive channels.
Figure 4:
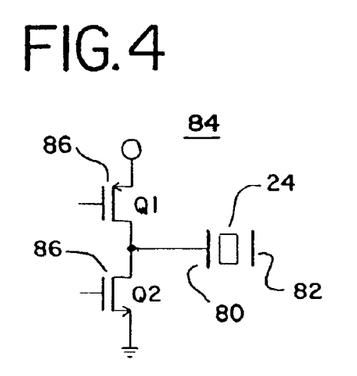
FIG. 4 is a circuit diagram of one embodiment of a transmitter.
Figure 5:
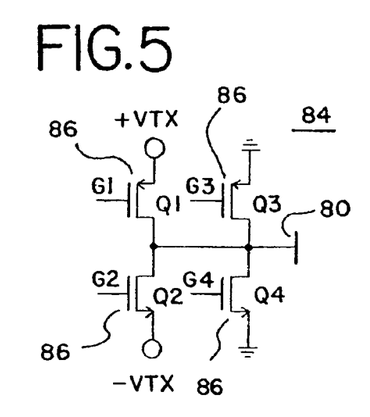
FIG. 5 is a circuit diagram of an alternative embodiment of a transmitter.

Faster or more complex two-dimensional and three-dimensional ultrasound imaging is provided by using multiplexing from a probe. A multiplexer is provided within a probe so that information from multiple transducer elements are multiplexed onto one signal channel for transmission to a base unit or ultrasound system for further processing. To avoid having different systems for different types of transducers, receive circuitry of an ultrasound system is operable in different modes based on the format of signals provided by the transducer. Different transmit pulsers may be used, such as the pulser shown in FIG. 12. Alternatively, transmit and receive path separation, such as shown in FIGS. 3–5 are used. To further minimize the number of channels connecting a probe to an ultrasound system without adversely affecting the size of the probe, a transmit channel is separated from the receive channel by a transducer element. This separation isolates the transmit channel while minimizing integration of high voltage devices within the probe. To allow the element to isolate the transmit and receive channels, the transducer array is manufactured from separately diced modules, each module including signal traces to opposite sides of each element.

The transmit pulser developments discussed above for multiplexing may be used independent of the multiplexing or other features. These independent developments or features are described in four general sections below. Receive circuitry for receiving information associated with different signal formats or for receiving just multiplexed format is described first. Isolation of the transmit path from the receive path using a transducer element and associated methods of use are described second. Third, an alternative transmit pulser connected with a receive amplifier without a dedicated transmit/receive routing switch is described. Finally, transducer arrays and methods of manufacture are described.

Figure 1:
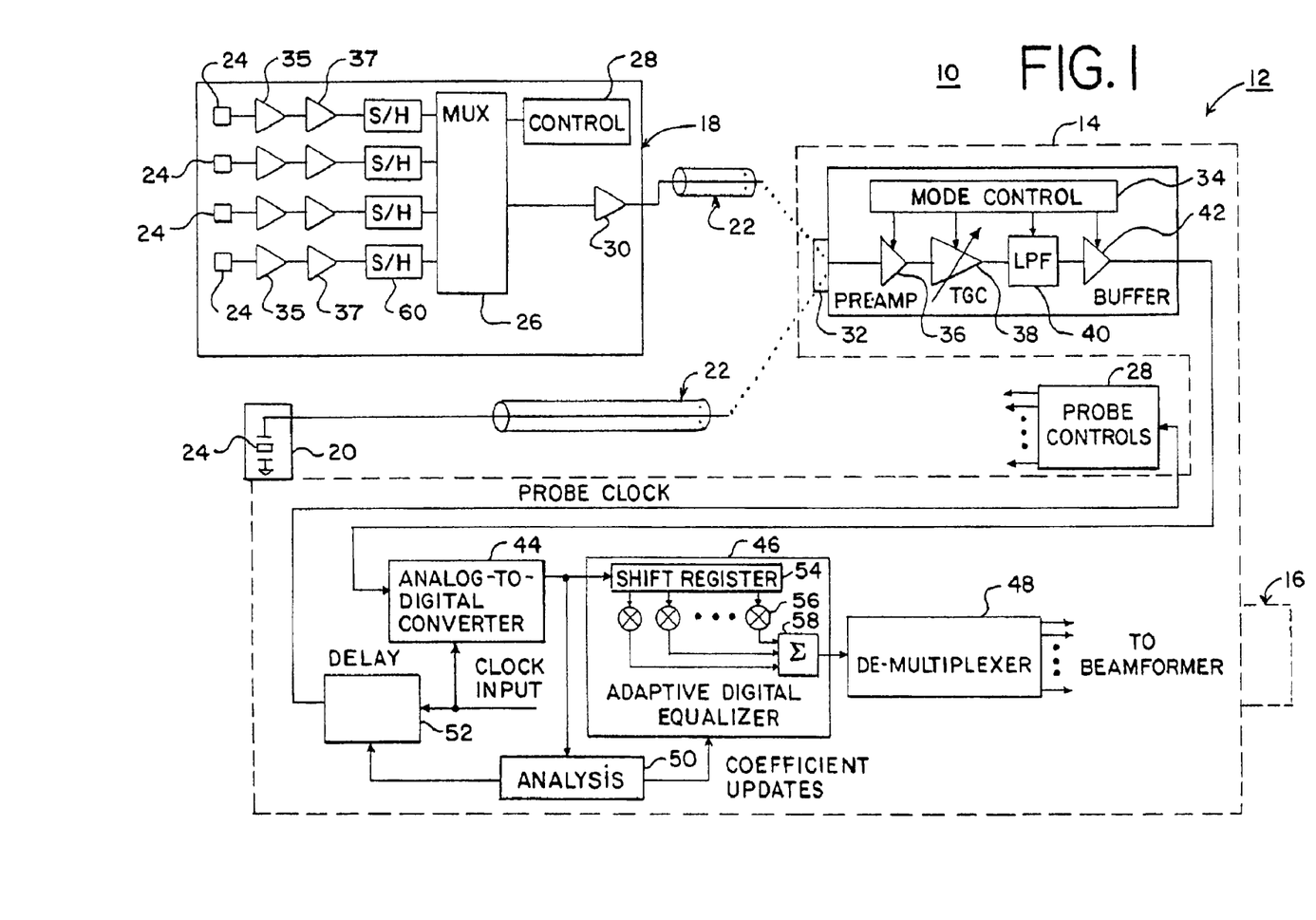
FIG. 1 is a block diagram of one embodiment of an ultrasound system for receiving different types of signals from different transducer probes.

Receive Circuitry:

FIG. 1 shows a block diagram of one embodiment of an ultrasound system 10. The system 10 includes a base unit 12 with receive circuitry 14 and an image processor 16. The receive circuitry 14 is operable to connect with different types of transducer probes 18, 20 via a cable 22. A plurality of receive circuits 14 are electrically connectable with the probes 18, 20 for processing signals from an array of elements 24. Additional, different or fewer components may be provided in the system 10, such as providing only one type of transducer probe 18, 20.

One transducer probe 20 comprises an array of piezoelectric or microelectromechanical elements 24 for transducing between acoustic and electrical energies. The probe 20 includes a single element, a linear array of elements or a multi-dimensional array of elements. The probe 20 also includes a housing covering the array. The housing is shaped to be a hand-held device or may be shaped for insertion into cavities or cardiovascular system of a patient. The probe 20 connects to the receive circuitry 14 using a cable 22 for each element 24 of the array. Each cable 22 transmits an analog signal representing the acoustic energy received at a single element 24. The signaling provided on the cable 22 from the probe 20 are conventional signals free of multiplexing or other intermediate circuits between the element 24 and the connector 32. The probe 20 provides signals or other information formatted differently than the signals from probe 18.

The probe 18 includes a linear or multi-dimensional array of elements 24 connected with a multiplexer 26. In one embodiment, 1,536 elements 24 are configured as a two-dimensional or multi-dimensional array. The probe 18 also includes a housing covering the array. The housing is shaped to be a hand-held device or may be shaped for insertion into cavities or cardiovascular system of a patient. In one embodiment, the transducer probe 18 comprises multi-dimensional transducer probe manufactured as discussed below using modules, but other linear or multi-dimensional arrays using a ground plane or with separate signaling made from one PZT component or modules may be used.

The probe 18 includes preamplifiers 35 and time gain controls 37 as a receive channel 64 prior to multiplexing. The receive channel 64 connects with the element 24. The preamplified and time gain controlled information are provided to sample and hold circuits 60. The sample and hold circuit 60 comprise analog delays for multiplexing analog information from multiple elements 24 onto one output. In the preferred embodiment, no sample and hold function exists. Analog waveforms are interleaved in time with no "hold" and no "analog delay" operation. Use of a sample and hold is not a requirement but it is one possible alternative.

In one embodiment, the receive circuits in the probe 18 dissipate less than 5 watts. In one embodiment, one multiplexer 26 is provided for every eight elements 24, but a single multiplexer may be provided for all elements or for a different number of elements. The multiplexer 26 comprises an analog or digital network of switches responsive to a probe control 28. In one embodiment, the multiplexer 26 combines signals from a plurality of elements 24 using time division multiplexing. In alternative embodiments, frequency multiplexing or other multiplexing schemes now known or later developed may be used. The probe control 28 controls the multiplexer 26 in response to a clock signal so that analog signals from each of the elements are assigned a specific time slot within a frame of time division multiplex information. In one embodiment, the probe 18 and associated multiplexer 26 comprise the time division multiplexing probe discussed in U.S. Pat. No. 5,622,177, the disclosure of which is incorporated herein by reference. Additional, different or fewer components may be provided in a probe 18, such as providing additional amplifiers or filters in the probe 18 or a probe free of the preamplifiers or time gain controls.

The multiplexer 26 outputs time division multiplex or other formatted data to a line driver 30. The line driver 30 comprises an amplifier or other device integrated with or separate from the multiplexer 26 for transmitting the multiplexed information over the cable 22. Separate cables 22 may be provided for additional multiplexers 26, such as 192 or 256 cables 22.

The base unit 12 comprises an ultrasound imaging system, such as a handheld, cart based or other system for generating a two-dimensional or three-dimensional representation of a patient. The receiver circuitry 14 receives information from one or more transducer probes 18, 20 for beamformation, detection and other ultrasound image processing by the image processor 16.

The receive circuit 14 includes a connector 32, a mode control processor 34, a preamplifier 36, a time gain control circuit 38, a low pass filter 40, a buffer 42, an analog-to-digital converter 44, a digital equalizer 46, a digital demultiplexer 48, an analysis processor 50, and a selectable delay 52. Additional, different or fewer components may be provided. The receiver circuit 14 comprises one or various combinations of two or more of the components described above. For example, the receiver circuitry comprises just the preamplifier 36 or just the low pass filter 40. The receive circuit 14 is operable with the transducer probe 20 where the signals from elements 24 may or may not be amplified and/or processed before transmission to the base unit 12. A second mode of operation allows transmission of time division or other multiplexed signals representing a group of elements along one signal line or cable 22. The receive circuitry 14 comprises a single receive channel within the base unit 12. Multiple receive channels for association with different cables 22 and different elements 24 are provided.

The connector 32 comprises a female or male latch with electrical contacts for connecting with a bundle of cables 22. The connector 32 is operable to connect with different transducer probes 18, 20. For example, a probe with time division multiplexing capabilities is connected to the connector 32. As another example, the probe 18 is disconnected from the connector 32 and the other probe 20 is connected to the connector 32. The connector 32 releasably maintains physical and electrical contact with the bundle of cables 22. In alternative embodiments, a separate connector 32 is provided for different probes 18, 20. The same base unit 12 and receive circuit 14 may be used for receiving and processing information from different types of transducer probes 18, 20. For example, the connector 32 connects with the probe 18 for imaging using a fully populated two-dimensional or 1.5 dimensional array. Time division multiplexing allows for steering in two spatial dimensions for two-dimensional or three-dimensional imaging while minimizing the number of cables 22 for communicating signals to the base unit 12. The same connector 32 connects with the other transducer probe 20 for ultrasound imaging using signals free of multiplexing. In one embodiment, multiple connectors 32 are provided with relay or solid-state switching into the common receive circuit 14 to provide rapid access to a selection of transducers. Each individual connector 32 may accept either multiplexed transducers 18 or conventional transducers 20.

The mode control processor 34 comprises a control processor, general processor, application specific integrated circuit or other analog or digital device for controlling components of the receive circuit 14, such as the preamplifier 36 and low-pass filter 40. In response to a configuration entered by the user, in response to control signals provided by the probe control 28, in response to a detection by the connector 32 of a type of probe, or in response to analysis of signals received from the ultrasound probe 18, 20, the mode control processor 34 configures one or more components of the receive circuitry 14 for processing in accordance with the type of data or data format provided by the probe 18, 20. The characteristics of the receive circuit are configured as a function of the data format.

The preamplifier 36 comprises transistors or other analog or digital devices for providing a low noise, wide band matched receiver. The preamplifier 36 is programmable or responsive to the mode control processor 34 for programming characteristics of the preamplifier. For operation with the transducer probe 20 or operation with signals representing a single transducer element 24, the preamplifier 36 is programmed to have a impedance characteristic similar to or at the impedance of the element 24 and the cable 22, such as 1 kOhm impedance. The impedance matches a generalization based on expected variations in cable impedances for different types of probes 20. The preamplifier 36 may alternatively be programmable for specifically matching specific types of probes 20 with different cables 22, cable lengths or elements 22. Preamplifier input impedance, gain and frequency response may be controlled either by selectable switched components or by altering preamplifier bias current. In practice, both methods may be employed simultaneously within an integrated circuit realization. For operation with multiplexed signals, the preamplifier 36 is programmed for an impedance match to the line driver 30 or other output circuitry of the probe 18. For example, the preamplifier 36 is programmed to provide an approximate 50 ohms impedance match. In alternative embodiments, different preamplifiers 36 are selected by the mode control processor.

In another embodiment, the gain characteristic of the preamplifier 36 is selected as a function of the format of signals or type of probe 18, 20. Multiplexed transducers 18 may require lower preamplifier gain than conventional transducers 20 because signals are already preamplified within the transducer prior to multiplexing. Also, noise performance of the system preamplifier 36 is not as stringent for multiplexed transducers 18 with integral preamplifiers 36, so a degraded noise preamplifier might be desirable to save power or otherwise optimize input impedance, gain, and frequency response.

Another programmable characteristic is the bandwidth of the preamplifier 36. For multiplexed information, the preamplifier 36 is not band limited or operates over a wide band, such as passing frequencies having a symbol rate of more than twice the center frequency of the transducer array (e.g., more than 5 MHz, 30 MHz or 100 MHz or more) for time division multiplexing. For information free of multiplexing, the bandwidth may be 2–15 MHz, such as associated with ultrasound frequencies or the frequency band of the transducer. Other characteristics of the preamplifier 36 may be adapted or altered as a function of the data format provided from the transducer probe 18, 20.

Signal conditioning blocks may be included in the multiplexer 26 or with the preamplifier 36 to provide pre- and post-equalization for frequency dependent losses in the cable 22. In alternative embodiments, the digital equalizer 46 provides post-equalization. The equalization may minimize inter-symbol interference. For example, pre-emphasis or high-frequency boost could be applied prior to driving the cable to compensate for frequency-dependent cable losses. An all-pass phase correction filter could also be implemented in the system receiver 14 to further reduce inter-symbol interference prior to the ADC.

The time gain control 38 (i.e. depth gain control) comprises an adjustable gain amplifier for variably amplifying analog signals. For signals representing a single element 24, the variable gain comprises a 40 to 80 dB range, but other gains may be used to account for the approximately one dB per MHz per centimeter of depth attenuation of ultrasound signals. The time gain control 38 operates the same or differently for multiplexed signals. Where a time gain control 38 is provided in the probe 18, the time gain control 38 of the receive circuit 14 provides less or no variable gain for multiplexed signals. Where the time gain control 38 applies a variable gain, the application of the gain accounts for the time division multiplexing by applying a same gain within each frame of signals from multiple elements 24.

The low-pass filter 40 comprises an anti-aliasing filter implemented as a finite impulse response or infinite impulse response filter. The low-pass filter 40 band limits signals so signals greater than ½ the digital sampling rate do not alias into the signal spectrum. By lowering the bandwidth of the low-pass filter, a greater signal-to-noise ratio is provided as long as signals of interest are not removed or reduced. Signals of interest provided by the probe 20 or representing a single element 24 are provided in a 2–15 MHz frequency range. The low-pass filter 40 is programmed with a 6 dB down or other cutoff frequency of 30 MHz, 15 MHz less or other frequency. The bandwidth may be programmed as a function of the type of imaging or type of probe 20 used. For multiplexed signals, such as time division multiplex information, the bandwidth is greater to pass multiplexed signals while minimizing inter-symbol interference. For example, the bandwidth is 30 MHz or greater, such as 50 or 100 MHz, to provide a Nyquist channel shape or a linear-phase low-pass filter with the following magnitude response symmetry: $|H(f)|=1-|H(Fsample-f)|$, for $0<f<Fsample$, where Fsample is the multiplexed sample rate (e.g. 96 MHz). In practice, $H(f)$ is an approximation to a Nyquist channel and errors are corrected via the digital equalizer 46.

The buffer 42 comprises an amplifier or other analog components for buffering signals input to the analog-to-digital converter 44. The buffer 42 provides the same characteristics regardless of the type of data or data format used, but may provide programmable characteristics that differ as a function of data format. For example, faster slew rate may be required from 42 for multiplexed data. A programmable slew rate limit could be used to conserve power in non-multiplexed modes.

The analog-to-digital converter 44 samples the analog signals and outputs digital representations in any one of various now known or later developed codes. For data representing a single element 24, the analog-to-digital converter 44 samples the data in response to a clock input but without reference to other timing information. For time division multiplex data, the analog-to-digital converter clock input is synchronized with the multiplexer 26. The synchronization allows proper separation of signals from each of the different elements 24 with minimized cross signal interface.

The digitized samples are provided to an adaptive digital equalizer 46. The digital equalizer 46 comprises a programmable finite impulse response filter, such as implemented using a shift register 54, multipliers 56 and a summer 58. In alternative embodiments, a processor or other device is used to implement the equalizer 46. The digital equalizer 46 filters time division multiplex information to remove inter-symbol interference. The filter coefficients applied to the multipliers 56 are based on a transfer function or generation of inter-symbol interference from the element 24 through various stages or components of the receive circuit 14 that operate on the analog signal. In one embodiment, the filter coefficients are programmable to allow for adaptations or variations in the transfer function. The coefficients are selected in response to a test signal or other data processing accounting for detected differences in the transfer function, such as caused by different probes 18, different processing characteristics of analog components of the receive circuit 14 or changes due to time and temperature. For signals representing a single element 24 or signals free of multiplexing, the digital equalizer 46 passes the signals, such as providing no delay in a single tap with a multiplier coefficient of one.

The demultiplexer 48 comprises a digital demultiplexer, such as a network of switches for separating signals from various time slots in a frame of time division multiplex information. The demultiplexer 48 operates as a conditional demultiplexer. The receive signals are digitally demultiplexed. For example, the demultiplexer outputs signals from different elements 24 on different outputs for beam formation and other image processing by the image processor 16. For conventional signals or signals free of multiplexing, the demultiplexer 48 passes the information to the image processor 16 for beam formation.

The optional analysis processor 50 comprises a digital signal processor, a general processor, an application specific integrated circuit, analog components, digital components and combinations thereof for synchronizing the analog-to-digital converter 44 with the multiplexer 26 or selecting coefficients for the digital equalizer 46. The analysis processor 50 operates on a test signal. The probe control 28 causes the multiplexer 26 to transmit a known or predetermined digital or analog test signal through the cable 22 and receive circuit 14 to the analysis processor 50.

The test signal is transmitted as part of a calibration function, such as in response to user input or connection of the probe 18 to the connector 32. The base unit 12 commands or the probe control 28 automatically generate the test signals. In alternative embodiments, test signals are transmitted periodically. For example, a test signal is transmitted in a preamble or header for each frame of time division multiplexed information. One or both of synchronization and adaptive equalization are provided in response to periodic transmission of the test signals. For stability, some phase sensitive acquisition sequences, such as acquisition for Doppler processing, minimize or do not provide any adaptation or changes in phasing through synchronization or the equalization.

One or both of multiplexing or processing of the receive signals is adapted in response to the analysis of the test signal. For example, the operation of the multiplexer 26 is adapted to the operation of the analog-to-digital converter 44 by synchronizing clock signals. The analysis processor 50 selects a selectable delay 52 for phasing the clock signal provided to the multiplexer 26 in reference to the analog digital converter 44. Fixed delays in clocking circuitry, variable delays due to clock signal path lengths, multiplexer circuit delays, multiplex signal path length, group delays and amplifiers and digitization of delays cause misalignment, resulting in mixing signals from different elements 24 by the analog-to-digital converter 44. These misalignments may vary as a function of the probe 18, the receive circuit configuration, time, temperature and processes. The analysis processor 50 determines the beginning of each frame by detecting a known pattern or the test signal. Using the selectable delay 52, the phase of the clocking signals applied to the analog-to-digital converter 44 and the multiplexer 26 are synchronized. In alternative embodiments, the analogto-digital converter clock signal is phased relative to the clock signal provided to the multiplexer 26, or a group or subgroup of receive circuits 14 are used to determine the phase of a clock signal common to more than one multiplexer 26 relative to another clock signal common to more than one analog-to-digital converter 44. The adaptive clock adjustments simplify the multiplexing control circuitry and interface between the receive circuit 14 and the probe 18. One clock line or cable 22 is provided without additional and separate phasing information. In alternative embodiments, separate clock and phasing signals are provided to the probe controls 28.

In one embodiment, the processing by the receive circuit 14 is altered or adaptive as a function of the test signal by the analysis processor 52. For example, the analysis processor 50 selects coefficients from a lookup table or calculates coefficients for use by the digital equalizer 46. The digital equalizer provides symbol alignment or removal of intersymbol interference. The analysis processor 50 compares a known or stored test signal to the received test signal. Differences between the received test signal and the stored test signal are used to select coefficients. The coefficients are selected so that the receive signals are undistorted or intersymbol interference removed or diminished. In alternative embodiments, results from more than one analysis processor 50 are used to select coefficients for use by the digital equalizer 46.

In one embodiment, the receive circuit 14 includes a transmit receive switch. In alternative embodiments discussed below, no transmit and receive switch is provided.

Figure 2:
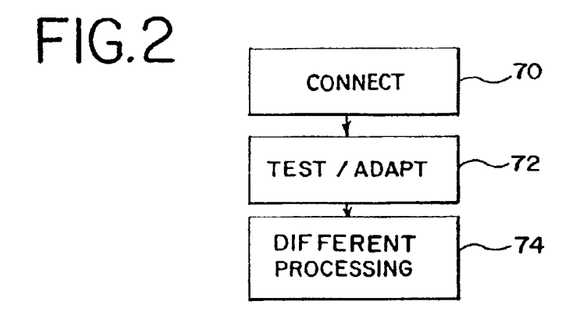
FIG. 2 is a flow chart diagram of one embodiment of a method for receiving data associated with a plurality of transducer elements on a single cable.

FIG. 2 represents a flow chart of one embodiment of operation of the system 10 of FIG. 1. In act 70, one of various possible probes 18, 20 are connected with a base unit 12. One of the probes 18, 20 is selected and attached to the connector 32. For example, a user desires three-dimensional cardiac imaging, so a two-dimensional array of elements in the probe 18 associated with time division multiplexing is connected.

For probes associated with multiplexing, a test signal is transmitted in act 72. Multiplexing or processing are adapted in response to the test signal. For data free of multiplexing, act 72 is optional or not provided. The test signal is transmitted in response to connection of the probe 18, response to control signals from the receive circuitry 14, in response to user input, automatically, or periodically. For example, a test signal is transmitted as part of an initial calibration process or is transmitted periodically in the header of first time slot or other slot of each frame of time division multiplex information. The received test signal is compared to an expected test signal. In response to comparison, equalization coefficients or other processing of the receive circuit is adapted or altered. Additionally or alternatively, the timing of the test signal is identified and selectable delays determined for synchronizing the analog-to-digital converter 44 with the multiplexer 26.

In act 74, the receive circuitry 14 is configured to have different characteristics as a function of the type of probe or format of the data received from the probe 18, 20 connected with the receive circuitry 14. Where the data format corresponds to multiple elements, such as time division multiplexed data, the information is processed in response to different impedance, gain, filtering, equalization, analog to digital conversion or other processes than for data associated with a single element or free of intervening circuitry in the probe 20. Any one or combination of two or more of the various characteristics may be altered as a function of the data format. Additional or different characteristics may also or alternatively be altered. Act 74 may be performed before or after act 72.

The analog information is then digitized. For time division multiplex information, the analog-to-digital converter 44 is synchronized with the multiplexed information. The multiplexed information is then demultiplexed for beamformation and other imaging processes.

Transmit and Receive Isolation:

A transducer element 24 may be used to isolate the transmit channel from the receive channel in either of the probes 18, 20 discussed above or another probe for use with different receive circuits. While useful for single element transducers, linear arrays, or arrays with limited or no transmit or receive circuitry within the probe, using a transducer element 24 to isolate the transmit and receive channels is particularly useful for multi-dimensional transducer arrays with at least part of transmit, and/or receive circuitry incorporated within the probe, such as discussed above for the time division multiplexing probe 18. A fully populated multi-dimensional transducer array requires a large number of transmit and receive channels. By placing transmit or receive circuitry within the probe and providing multiplexing, the number of cables 22 or channels from the probe 18 to the base unit 12 are minimized. However, the transmit and receive circuitry then coexists in a small space, making isolation of the receive circuits from the high voltages of the transmit circuits difficult. High voltage switches, such as switches able to withstand 200 volts of reverse voltage, are difficult to integrate with other receive circuits, such as a multiplexer. High voltage transmit and receive switching is replaced with the transducer element for isolating the transmit channel from the receive channel.

FIG. 3 shows a transducer element 24 isolating or separating a transmit path 62 and a receive path 64. Direct connection between the transmit path 62 and the receive path 64 is avoided. The element 24 isolates the paths 62, 64 to allow high voltage transmission without subjecting the receive path 64 to the high voltage. High voltage devices are provided as part of the transmit path 62 but not as part of the receive path 64 in one embodiment. In alternative embodiments, high voltage devices are provided on the receive path 64.

The element 24 comprises one of a plurality of elements in a multidimensional or linear array. 1.5 dimensional and 2-dimensional arrays may be represented as multidimensional arrays of a N×M grid of elements where both N and M are greater than 1. For multi-dimensional arrays, the elements may be small and have a high impedance as compared to elements 24 of a linear array. Parasitic loading associated with a cable 22 is also absent or reduced for use with a multiplexer and the probe 18. A smaller transmit pulser and very low power receive preamplifier may be used given the high element impedance than for a lower impedance.

The element 24 includes two electrodes 80 and 82. The electrodes 80 and 82 are on opposite of the element 24, such as being on a top and bottom of the element on a range dimension. The electrode 80 is free of an electrical connection with the electrode 82. Separate signal traces comprise or connect with each of the electrodes 80 and 82. Each element 24 is associated with two or more separate signal traces for associated separate electrodes 80, 82. In alternative embodiments, two or more electrodes share a same signal trace. One electrode 80 connects to the transmit path 62, and the other electrode 82 connects to the receive path 64. The element 24 is free of an electrical connection directly to ground, such as provided by an electrode connected directly to ground.

The transmit path 62 connects with the electrode 80 for applying a transmit waveform to the element 24. The transmit path 62 comprises at least one signal trace to element 24 within the probe 18. In other embodiments, additional transmit circuitry, such as a waveform generator 84, a switch driver 87, and a controller 88 are incorporated within the transmit path 62 and within the probe 18. In alternative embodiments, the controller 88, the driver 87, the waveform generator 84 or combinations thereof are positioned external to the probe 18, such as within the base unit 12.

The waveform generator 84 comprises one or more high voltage transistors, such as FET transistors, for generating unipolar, bipolar or sinusoidal waveforms. One embodiment of a transmit waveform generator 84 for generating a unipolar waveform is shown in FIG. 4. Two high voltage transistors 86, such as CMOS FET transistors with at least a withstand of 200 volts connect in series between a voltage source and ground. In one embodiment, one transistor comprises a PFET, and the other transistor comprises an NFET. The transistors 86 provide high voltage and ground driving of a unipolar waveform at the electrode 80. Since the transmit waveform generator 84 comprises a switch mode device, power dissipation is minimal. This circuitry for each element 24 uses about 0.2 millimeters$^2$ of die area. For a 2-dimensional array of 1,536 elements, about 307 millimeter$^2$ of die area is used. Other integration formats may be provided, such as providing groups of high voltage FET transistors in smaller application specific integrated circuits. In alternative embodiments, other devices, such as digital-to-analog converters, are used for waveform generation.

FIG. 5 shows a network of transistors 86 for generating a bipolar waveform. Four transistors 86 allow generation of a bipolar waveform ending with a positive voltage, negative voltage, or zero voltage. Three transistors 86 may be used if the bipolar waveform is capable of ending at only one polarity, such as a positive voltage. Of the transistors, Q1 and Q2 of FIGS. 4 and 5 may have an integral reverse diode from the drain to the source, but transistors Q3 and Q4 avoid the reverse diode configuration to avoid conducting through the diodes. Other configurations and networks of transistors 86 may be used.

Each of the transistors 86 connects to a reference voltage, such as a positive voltage, a negative voltage or ground. As shown in FIG. 4, one transistor 86 connects to ground and the other transistor 86 connects to a positive or negative voltage. As shown in FIG. 5, two transistors 86 connect to ground, one transistor connects to a positive voltage, and another transistor connects to a negative voltage.

The driver 87 comprises a transistor or FET driver for controlling operation of the waveform generator 84. In alternative embodiments, other drivers may be used. The driver 87 is integrated as part of an application specific integrated circuit, but may have separate devices or comprise a general processor. The driver 87 is operable to provide voltage changes for operating the transistors 86. For example, the transistor Q2 of FIG. 4 is controlled by application of a 10 volt or 0 volt signal from the driver 87. The transistor Q1 is controlled by application of a 200 volt or 190 volt signal from the driver 87.

The controller 88 comprises a general processor, analog components, digital components, application specific integrated circuit, or combinations thereof for controlling one or more drivers 87 associated with one or more elements 24. In one embodiment, the controller 88 is integrated on the same application specific integrated circuit as the driver 87, but may be a separate device. The controller 88 outputs binary signals to control the operation of the driver 87 and waveform generator 84. The controller 88 in one embodiment extrapolates or selects transmit configurations or waveform parameters for an entire array or sub-array based on simple control signals provided from external to the probe 18. In alternative embodiments, the controller 88 is located external to the probe.

The receive path 64 comprises at least a single signal trace connected with the electrode 82 on an opposite side of the element 24 from the transmit path 62. In other embodiments, the receive path 64 includes one or more of diodes 90, 92, preamplifier 94 and a multiplexer 96. Additional, different or fewer circuits may be provided as part of the receive path 64, such as a filter. The electronics may not contain an explicit filter in the probe where the transducer element itself may be sufficient and/or the natural low-pass response of the amplifier is sufficient to filter the receive signal. The receive path is included within the probe 18 with the element 24. In alternative embodiments, a multiplexer is not provided and the preamplifier 94 is provided in a base unit 12 separate from the probe 18 or in the probe 18. A cable 22 connects the receive path 64 to the base unit 12.

The diodes 90 and 92 comprises Schottky diodes or other high current, low voltage diode devices. In one embodiment, the diodes 90 and 92 are free of quiescent power dissipation. Each of the diodes 90 and 92 connects to ground with an opposite or different polarity. The diodes 90 and 92 comprise a diode clamp to limit voltage swings on the receive path 64 at the electrode 82. For example, the diodes 90 and 92 limit voltage transitions to between plus or minus 0.2 to 0.7 volts. In alternative embodiments, transistors or other devices are used for limiting the voltage at the electrode 82.

In one embodiment, the diodes 90 and 92 are integrated in an application specific integrated circuit with the preamplifier and multiplexer circuits 94 and 96. Other integration formats may be provided, such as providing discrete diode arrays and separate preamplifier/multiplexer circuits in smaller application specific integrated circuits.

The preamplifier 94 comprises one or more transistors for amplifying a signal from the electrode 82. For example, a differential BJT pair with current outputs are provided using a 7 volt BiCMOS process or other transistor process. Using 20 low $\mu$A per channel with a 5 volt supply allows a consumption of 0.1 milliwatts per channel. Other preamplifiers with different power consumptions and associated components and characteristics may be used. The preamplifier 94 may alternatively or additionally include a time or depth gain control amplifier or a filter. For a time gain control amplifier integrated within the probe 18, a low power device for providing some but not all of the time gain compensation may be used. In alternative embodiments, a larger, more power consuming variable amplifier is provided.

The multiplexer 96 comprises a network of switches, such as transistors and analog sample and hold circuits for multiplexing the signals of a plurality of transmit paths 64 onto one cable 22. For example, the multiplexer 96 comprises an 8 to 1 multiplexer for multiplexing signals from 8 different elements 24 into one frame of analog information. In one embodiment, the multiplexer 96 is operable to provide 12 MSPS for each receive path 64 for a total of 96 MSPS for 8 receive paths 64. The circuitry of the receive path 64 is free of high voltage devices and may be integrated into one application specific integrated circuit or other general circuit in a small space within the probe 18.

Figure 6:
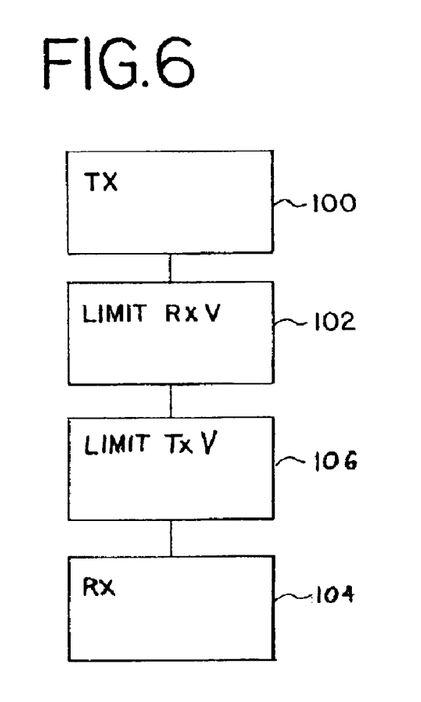
FIG. 6 is a flow chart diagram of one embodiment representing use of the isolated transmit and receive channels of FIG. 5 to transmit and receive acoustic information.

Connecting the transmit and receive path 62 and 64 to opposite electrodes 80 and 82, respectively, isolates the high voltages and high voltage devices of the transmit path 62 from the low voltage devices of the receive path 64. FIG. 6 shows a flow chart of one embodiment for transmitting and receiving using the element 24 of FIG. 3. In act 100, a high voltage transmit waveform is provided to the transducer element 24, and the voltage in the receive path 64 is limited in act 102. Subsequently, the voltage on the transmit path 62 is limited in act 106 and echo signals are received on the receive path 64 in act 104.

The transmit and receive operation of the element 24 is free of switches to select between the transmit and receive path 62 and 64. In response to control signals from the controller 88, the driver circuit 86 causes the waveform generator 84 to generate a high voltage (e.g., 200 volt) transmit waveform in act 100. Where the waveform generator 84 is positioned within the probe 18, the transmit waveform is generated within the probe 18. The transmit waveform is applied to one electrode 80 of the element 24. The voltage of the other electrode is limited, effectively acting as a ground or D.C. reference, in act 102. The diodes 90 and 92 clamp the voltage of the receive path 64 connected to the electrode 82 to within a small voltage range as compared to the high voltage of the transmit waveform. In response, the element 24 generates an acoustic signal due to the potential difference across the electrodes 80 and 82. The element 24 also isolates the transmit path 62 from the receive path 64, preventing damage to receive circuitry without high voltage switching.

For a subsequent receive operation of act 104, the voltage at the transmit path 62 is limited. In one embodiment, a transistor 86 of the waveform generator 84 connects a ground or reference voltage to the electrode 80. For example, Q2 of the waveform generator 84 shown in FIG. 4 is switched "on" to ground the electrode 80. In an alternative embodiment, another reference voltage, such as a positive voltage applied through Q1 is connected to the electrode 80 to limit the voltage swing or change of the electrode 80. While the voltage of the transmit path and associated electrode is limited in act 106, electrical signals are generated at the electrode 82 in response to acoustic echo signals received by the element 24 in act 104. Since the electrical signals received are small, such as less than 0.2 volts, the diodes 90 and 92 avoid introducing noise within or clipping the receive signal. The receive signal is amplified, filtered, multiplexed, or otherwise processed for transmission over the cable 22 to the base unit 12. For example, the amplifier 94 preamplifies the signals and adjusts the gain of the electrical signals as a function of time. The multiplexer 96 multiplexes the electrical signals with other electrical signals responsive to different transducer elements 24. The same process is repeated for receive channels 64 associated with other elements 24. The transmit and receive operations are performed free of selecting between transmit and receive paths for connection with an electrode. Each of the transmit and receive paths 62 and 64 act to ground or otherwise maintain an electrode 80, 82 at a reference voltage during reception and transmission, respectively.

Using the waveform generator 84 shown in FIG. 4, unipolar waveforms may be generated ending either with zero voltage or a positive voltage. The unipolar waveform generator 84 is capable of ending on a positive or zero voltage state without damage to the circuit. An alternative embodiment would allow unipolar waveform generation between zero and a negative voltage by swapping the NMOS and PMOS devices and using a negative power supply. In either case a low impedance condition is provided whether the unipolar transmit waveform ends at a 0 voltage or other voltage.

Figure 7:
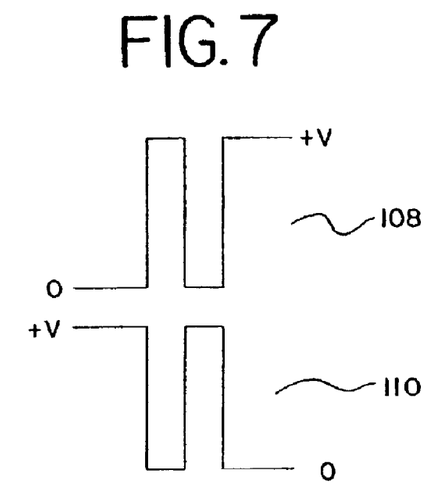
FIG. 7 is a graphical representation of unipolar pulses with opposite phases.

FIG. 7 shows two mirror symmetric unipolar waveforms 108 and 110. The first unipolar waveform 108 begins at a low state or zero voltage level, includes a positive voltage pulse, returns to a 0 voltage level and then ends at a high state or positive voltage level. The subsequent unipolar waveform 110 begins at a high state or positive voltage and ends at a low state or zero voltage. Since one waveform begins at the higher voltage and ends at the lower voltage and the other waveform 108 begins at the lower voltage and ends at the higher voltage with the same number of cycles, the two waveforms sum, to substantially a zero value. Substantially accounts for differences in rise and fall path times of the transistors 86 and other differences in performance using transmit waveforms beginning at different voltages. In alternative embodiments, the high state is zero volts and the low state is a negative voltage.

The mirror symmetric capability of the unipolar waveform generator 84 allows for tissue harmonic or other harmonic imaging using phase inversion with unipolar transmit waveforms. As acoustic energy responsive to the transmit waves propagates and scatters within tissue, energy at second harmonics or other harmonics of the fundamental transmit frequency is generated. The receive signals responsive to each of the unipolar waveforms include information at the fundamental frequencies as well as the harmonic frequencies. When the receive signals responsive to the phase inverted transmit unipolar waveforms are combined or added, information at the fundamental frequencies cancels, leaving information at harmonic frequencies.

Harmonic imaging in response to phase inversion of transmit waveforms is provided using simple unipolar waveforms. The transistors 86 used for generating the unipolar waveform are designed to avoid rise time and fall time mismatches, minimizing the amount of harmonic information introduced by the waveform generator 84. The material of the element 24 has a high poling voltage in one embodiment to minimize differences in operation or receive mismatches due to initial generation at two different DC bias points (e.g. 0 and +V). Transmission of a phase inverted unipolar pulses may be used with systems having a transmit channel within the base unit or within the probe, and with systems using transmit and receive switching.

Transmit Pulser with Receive Amplifier Interconnection:

A transmit pulser interconnected with a receive preamplifier without dedicated transmit/receive routing switches may be used in either of the probes 18, 20 discussed above or another probe for use with different receive circuits. While useful for single element transducers, linear arrays, or arrays with limited or no transmit or receive circuitry within the probe, using the transmit pulser directly interconnected with receive circuitry is particularly useful for multi-dimensional transducer arrays with at least part of transmit, and/or receive circuitry incorporated within the probe, such as discussed above for the time division multiplexing probe 18. A fully populated multi-dimensional transducer array requires a large number of transmit and receive channels. By placing transmit or receive circuitry within the probe and providing multiplexing, the number of cables 22 or channels from the probe 18 to the base unit 12 are minimized. However, the transmit and receive circuitry then coexists in a small space, making isolation of the receive circuits from the high voltages of the transmit circuits difficult. High voltage switches, such as switches able to withstand 200 volts of reverse voltage, are difficult to integrate with other receive circuits, such as a multiplexer. High voltage transmit and receive switching is replaced with the transmit pulser interconnected directly with receive circuitry for isolating the high voltage transmit devices from low voltage receive devices.

FIG. 12 shows one embodiment of a transmit pulser 300 with an interconnected receive circuit. High voltage transmission is provided without subjecting the receive circuitry to the high voltage due to the diode clamping at the receive preamplifier inputs. The transmit pulser 300 includes a quadraplexor or an H-bridge of switches or transistors 86 around a transducer element 24. In alternative embodiments, different transistor or other types of switches are used for one, multiple or all of the transistors 86. Two of the transistors 86 (e.g. Q2 and Q4) connect from different electrodes 80, 82 of the transducer element 24 to a power source 302. Two other transistors 86 (e.g. Q1 and Q3) connect from the different electrodes 80, 82 to different inputs of the differential receive preamplifier 94. The transistors 86 both with a connection to the power source 302 or different power sources are matched transistors 86 in one embodiment. The transistors 86 both with a connection to the receive preamplifier 94 are also matched transistors 86. For example, transistors Q2 and Q4 are P-channel High voltage FETs, PNP high-voltage bipolar or other transistors or switches with a withstand voltage of at least 100 volts, and transistors Q1 and Q3 are N-channel High voltage FETs, NPN high-voltage bipolar or other transistors or switches with a withstand voltage of at least 100 volts. In alternative embodiments, non-matched pairs of transistors 86 are used, such as using PFET and NFET transistors. For a given peak-to-peak drive voltage, the H-bridge (quadraplexor) configuration uses transistors with half the breakdown voltage. This is a potential advantage because either such transistors are cheaper or easier to manufacture, or with the same breakdown voltage may deliver twice the peak-to-peak drive.

The transducer element 24 is one of the elements 24 described herein. Likewise, the two electrodes 80 and 82 as described above are electrically separate. The electrodes 80 and 82 connect to the transistors 86 of the transmit pulser 300 as shown. The element 24 is free of an electrical connection directly to ground, such as provided by an electrode connected directly to ground.

Two diode clamps, each including a pair of diodes 90, 92 (e.g. Schottky diodes or other high current, low voltage diode devices), also connect between the differential inputs of the receive amplifier 94 and ground. Each of the diodes 90 and 92 connects to ground with an opposite or different polarity. The diodes 90 and 92 comprise a diode clamp to limit voltage swings on each of the inputs to the receive amplifier 94. For example, the diodes 90 and 92 limit voltage transitions to between plus or minus 0.2 to 0.7 volts, but higher limits, such as 1 to 2 volts due to different types of diodes or the drive current, may be provided. In alternative embodiments, transistors or other devices are used for limiting the voltage at the electrode 82.

The preamplifier 94 comprises a low voltage amplifier, such as one or more transistors for amplifying a signal from the electrode 82 fabricated from a low-voltage IC process. For example, a differential BJT pair with current outputs are provided using a 7 volt BiCMOS process or other transistor process. Using 20 $\mu$A per channel with a 5 volt supply allows a consumption of 0.1 milliwatts per channel. Differential amplifiers may be biased from relatively low voltage supplies and without large capacitors, making the preamplifier 94 of this embodiment easier to integrate. Other preamplifiers with different power consumptions and associated components and characteristics may be used. The preamplifier 94 may alternatively or additionally include a time or depth gain control amplifier or a filter. For a time gain control amplifier integrated within the probe 18, a low power device for providing some but not all of the time gain compensation may be used. In alternative embodiments, a larger, more power consuming variable amplifier is provided.

The drivers 87 comprises a transistor or FET driver, but other drivers may be used for controlling operation of the transistors 86. The drivers 87 are operable to provide voltage changes for operating the transistors 86. For example, the transistors 86 Q1 and Q3 are controlled by application of a 10 volt or 0 volt signal from the associated drivers 87. The transistors 86 Q2 and Q4 are controlled by application of a 200 volt or 190 volt signal from the associated drivers 87. A controller 88 as described above controls operation of the drivers 87.

While the element 24 may not isolate the transmit circuits from the receive circuits, the arrangement of the transmit pulser 300 allows separable integration of high voltage transmit devices and low voltage receive devices, such as providing the transistors 86, drivers 87, and/or control 88 for one or more elements 24 in one application specific integrated circuit and the diodes 90, 92, receive amplifier 94 and/or multiplexer 26 for one or more elements 24 in the same or a different application specific integrated circuit. Other integration formats may be provided, such as providing discrete diode arrays or providing groups of high voltage FET transistors in smaller application specific integrated circuits.

The power source 302 comprises a positive direct current voltage source. In alternative embodiments, the power source 302 comprises different sources with same or different characteristics for the connected transistors 86 (e.g. Q2 and Q4). In yet another alternative embodiment, the power source 302 is a negative voltage source and/or an amplitude modulated or alternating power signal is provided by the power source 302.

In one embodiment, the output of the receive amplifier 94 connects with a multiplexer. The receive amplifier 94 and the multiplexer are positioned in a probe and connect with a cable. The probe separate from a base unit. In alternative embodiments, the receive amplifier 94 is within the base unit or is within the probe with a connection with the cable free of multiplexing.

By providing the H-bridge of transistors 86 connected to both electrodes 80 and 82, a same transmit pulser 300 may be operable to provide either of bi-polar or uni-polar transmit waveforms. In alternative embodiments, two transistors 86, such as Q1 and Q2, are provided without the other two transistors 86 for providing only uni-polar transmit waveforms. One of the electrodes 80, 82 is grounded. In yet other alternative embodiments, additional, different or fewer components and connections are provided. As used herein, connected with includes both direct connections and connections with intervening components.

Where some or all of the components of FIG. 12 are provided in the probe, the probe includes a grounding or electrostatic shield. The electrostatic shield provides low sheet resistance to protect the patient from any electrical charge provided to the electrodes. Also, a matching layer positioned between any electrode 80, 82 and the patient electrically isolates the electrodes 80, 82 from the patient.

Figure 13:
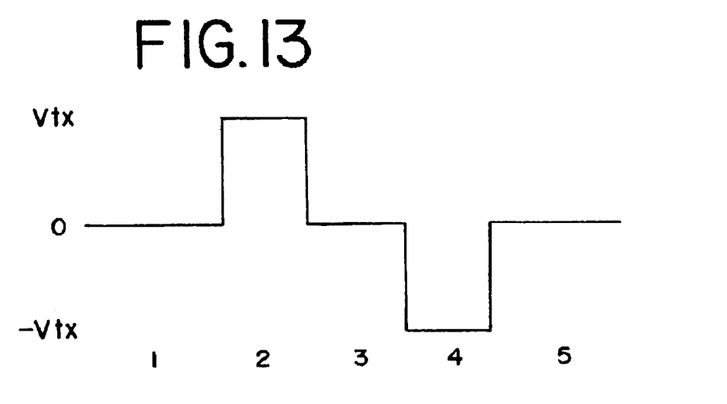
FIG. 13 is a graphical representation of a bi-polar transmit waveform of one embodiment.

The transmit pulser 300 connected as shown in FIG. 12 generates bi-polar transmit waveforms, such as shown in FIG. 13. During transmit operation, the transducer element 24 switchably connects to inputs of the receive amplifier 94 and switchably connects to the power source 302. The connections are performed alternately. All of the transistors 86 alternate between conductive and nonconductive states during transmit operation. For example, a first zero voltage state is provided by connecting the electrodes 80 and 82 to the inputs of the receive amplifier 94 and disconnecting the electrodes 80 and 82 from the power source 302 (e.g. Q1 and Q3 are on, and Q2 and Q4 are off). A positive voltage is provided by connecting the power source 302 to a positive electrode 82 and disconnecting the positive electrode 82 from the associated input of the receive amplifier 94 (e.g. Q1 and Q4 are on, and Q2 and Q3 are off). The diode clamp connected to the transistor 86 Q1 limits the voltage of the negative electrode 80 for generating the transmit waveform by a voltage difference across the element 24. A negative voltage is provided by reversing the connections for the positive voltage (e.g. Q1 and Q4 are off, and Q2 and Q3 are on). The diode clamp connected to the transistor 86 Q3 limits the voltage of the positive electrode 82 for generating the transmit waveform by a voltage difference across the element 24. The diode clamps limit the voltage provided to the receive amplifier 94, allowing use of low voltage components in the receive amplifier 94.

Where the transistors 86 comprise matched pairs of transistors, a substantially symmetrical transmit waveform is generated. Driving the transmit waveform to or from zero, positive and negative voltages is performed by substantially identical pairs of transistors. Since both electrodes 80 and 82 are used to generate the transmit waveform, a lower voltage power source 302 may be used as opposed to driving only one electrode 80, 82. The transistor breakdown voltages are also reduced by a factor of two.

A symmetrical transmit waveform minimizes the bandwidth of the transmitted waveform. Less energy is transmitted at the second or other harmonic frequencies by a symmetrical waveform than a non-symmetrical waveform. For imaging at harmonics of the transmitted frequency, transmission of energy at the harmonics is reduced or avoided. Propagation and reflection of energy to generate the harmonic information from tissue or contrast agents is better isolated by minimizing transmission of energy at the same or similar frequencies. In a further embodiment, harmonic imaging is provided using phase differences between transmit waveforms. By providing accurate timing, different transmit pulses are generated with different phases. The received energy is summed to cancel information at the fundamental transmit frequencies and maintain information at even (e.g. second) harmonic frequencies. Other combinations of transmit phase and receive combination may be used to isolate information at one or more fundamental and/or harmonic frequency bands.

Since the voltage applied to the electrodes 80 and 82 may be held by the diode clamps to a low voltage, the transmit pulser 300 may drive to a substantially zero transmit voltage. Bi-polar waveforms with at least part of the waveform being a substantially zero voltage may be used, such as for pulse width modulation as described in U.S. Pat. No. 5,833,614, the disclosure of which is incorporated herein by reference.

For receive operation, the power source 302 is disconnected from the electrodes 80 and 82. Due to the diode clamps, the inputs of the receive amplifier 94 are limited to the forward voltages of the diodes 90, 92. Receive signals are usually less than the forward voltages of the diodes 90, 92, so differential receive signals are input to the receive amplifier 94 by connecting the electrodes 80, 82 to the inputs of the receive amplifier 94. The receive signal is amplified, filtered, multiplexed, or otherwise processed for transmission over the cable 22 to the base unit 12. The transmit and receive operation of the element 24 is free of switches to select between the separate transmit and receive paths.

Multi-Dimensional Transducer:

Various transducers can be used with any of the transmit and receive paths, probes and receive circuits discussed above. Some such multi-dimensional transducer arrays for fully sampled use with time division multiplexing and element based isolation of transmit and receive paths is shown in FIGS. 8–11. Time division multiplexing reduces the channel count or number of cables 22 without limiting the beamforming performed by the base unit 12. Separate signal traces or connection of opposite electrodes 80 and 82 to transmit and receive path allows integration of transmit and receive circuitry in the probe 18 without power consuming transmit and receive switching. Various aspects of the multidimensional transducer may be used independent of other aspects of the embodiments described herein, such as using a particular element spacing without time division multiplexing or other integration of circuitry within the probe 18.

Figure 8:
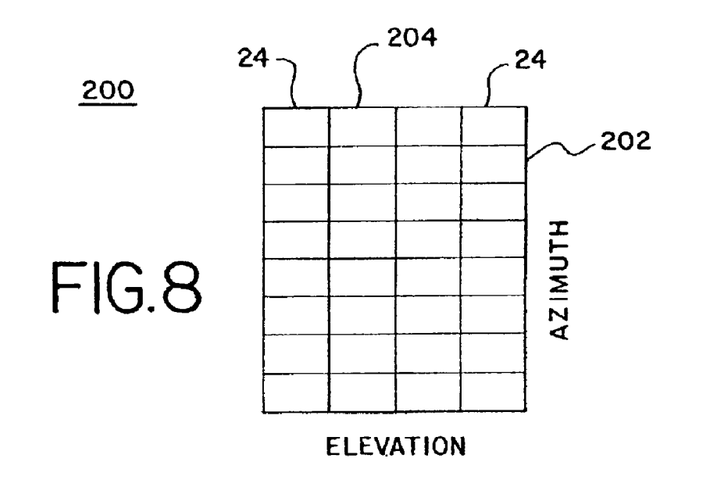
FIG. 8 is a graphical representation of a multi-dimensional transducer array.

FIG. 8 shows a 2-dimensional array 200 of elements 24. The elements 24 are spaced in a grid along the elevation and azimuth dimensions. A different or same number of elements 24 may be provided along the elevation dimension than along the azimuth dimension. A plurality of elements 24 are provided in columns 204 along the azimuth dimension. The elements 24 have a pitch or spacing along the azimuth dimension. In one embodiment, a ½ wavelength pitch is used. From the center of one element to the center of an adjacent element 24 along the azimuth dimension, a distance of ½ of a wavelength is provided. For example, in an array designed for operation at 2.5 MHz, the pitch is 300 micrometers. Other spacings, may be used.

The elements 24 are provided in rows 202 along the elevation dimension. The pitch or spacing along the elevation dimension is greater than the pitch or spacing along the azimuth dimension. In one embodiment, the pitch along the azimuth dimension is ⅔ or less, such as ½, than the pitch along the elevation dimension. For the 2.5 MHz center frequency array example given above, the pitch in elevation is 600 micrometers or one wavelength. For large pitches, each individual element may be sub-diced for proper operation or to maintain a desired ratio of the width to a thickness of the element 24. In the example provided above, the elements 24 are sub-diced along the elevation dimension, such as providing a dicing cut extending through about 90 percent of PZT material at the center of each array, but not sub-diced along the azimuth dimension. Other sub-dicing depths may be used.

FIG. 8 shows thirty-two elements 24. In alternative embodiments, different numbers of elements are provided, such as 1,536 elements in 64 azimuthally spaced rows 202 and 24 elevational spaced columns 204, or 2,048 elements in 64 azimuthally spaced rows 202 and 32 elevation spaced columns 204.

Figure 9:
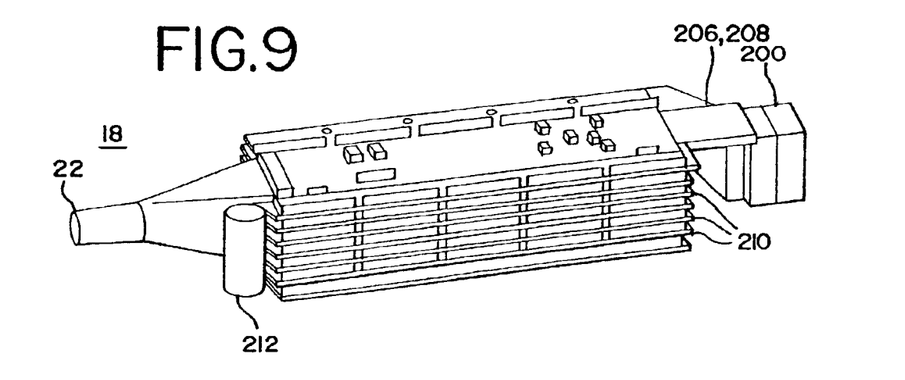
FIG. 9 is a perspective view of one embodiment of an interior of a probe including a multi-dimensional transducer array connected with circuit boards.

FIG. 9 shows a probe 18 integrating the array 200. The probe 18 includes the array 200, flexible circuit materials or signal traces 206, 208, a plurality of circuit boards 210, a capacitor 212 and a bundle of cables 22. These components are housed within a plastic or other ergonomically shaped probe cover or housing. Different, fewer or additional components may be included in the probe 18.

The flexible circuits 206, 208 comprise Kapton or other flexible, thin, electrical insulating material with deposited signal traces on one or two sides. Flexible circuit is used herein to describe any flexible or non-rigid material with one or more electrical conductors. In one embodiment, the flexible circuit material is 50 µm thick. Separate flexible circuit materials 206 and 208 are provided for separate transmit and receive paths. For example, one flexible circuit 206 provides electrodes and traces from one side of the elements 24 of the array 200, and the other flexible circuit 208 comprises of electrodes and traces from an opposite or different side of the elements 204 of the array 200.

Figure 10:
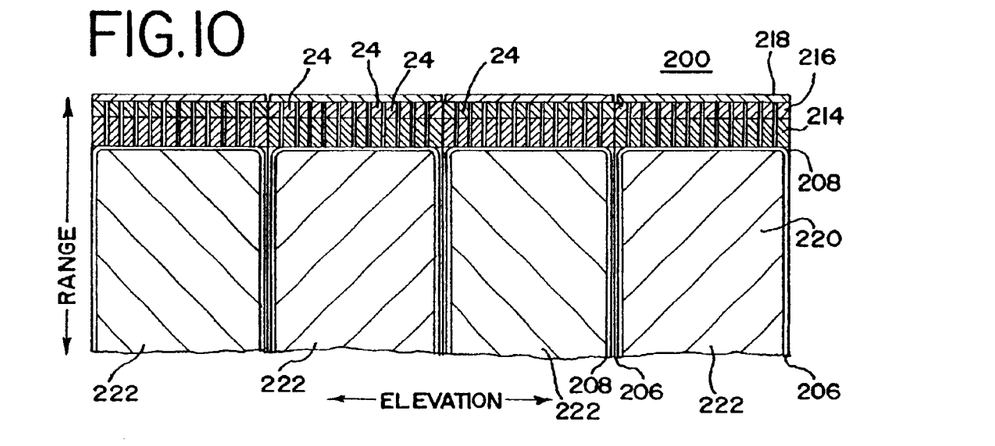
FIG. 10 is a cross sectional diagram of one embodiment of a multidimensional array assembled from modules.

FIG. 10 shows an elevation cross-section of the array 200 and the associated connections of the two flexible circuits 206 and 208. The array 200 is subdivided along the elevation dimension into four modules 222. Additionally, the array 200 may be subdivided along the elevation direction into different or fewer modules 222. For example, only one, two, three, or more modules may be used. Each module has an associated pair of flexible circuits 206 and 208. Each module 222 includes a plurality of layers along the range dimension, such as a first matching layer 218, a first electrode layer on the top of the element 24 formed from the first flexible circuit 208, a second matching layer 216, an element or piezoelectric (PZT) layer 214, a second electrode on a bottom side of the piezoelectric layer 214 formed from the second flexible circuit 208 and a backing material 220. Additional, different or fewer layers may be provided in one, more or all of the modules 222. For example, only one or three or more matching layers 216, 218 are used, or both matching layers 216 and 218 are on a top side of the top electrode and flexible circuit 208.

The two different flexible circuits 208 and 206 are folded along one or two sides of the modules from the PZT material or layer 214 towards and along the backing material 220. Separate signal traces are provided to each of the elements 24 on both sides or top and bottom of the elements 24. Separate signal traces are provided on the flexible circuit 206 for each of the elements 24, and separate signal traces are provided on the flexible circuit 208 for each of the elements 24. Each of the elements 24 independently connects with the separate signal traces on the top and bottom along the range dimension of the element 24. Separate signal traces allow for element based isolation of the transmit and receive paths. In alternative embodiments, a common ground connects with a plurality of elements 24.

The backing material 220 of each module 222 is separated from the other backing material 220 of another module 222 by two or four layers of flexible circuit 206, 208. The PZT layer 214 of one module 222 is separated by one or two flexible circuit layers 208 from the PZT layer 214 of another module 222. The width of the PZT layer 214 is greater than the width of the backing material 220 to account for the different thicknesses due to the different number of flexible circuits 206, 208. By having a thin flexible circuit material, adverse acoustic effects are avoided by minimizing the separation between elements 24 of different modules 222.

Referring again to FIG. 9, the flexible circuits 208 and 206 are shown as having an increasing width away from the array of elements 200. Increasing the width allows for greater separation of the signal traces from individual elements 24. The greater separation provides for less capacitive coupling between signal traces.

FIG. 9 shows a plurality of printed circuit boards 210, such as seven circuit boards 210. In alternative embodiments, a single circuit board 210, a different number of circuit boards 210 or no circuit board are provided in the probe 18. In one embodiment, six circuit boards 210 include transmit and receive circuitry, such as the probe integrated circuitry discussed above. Each transmit and receive circuit board 210 connects with one of six elevationally spaced modules 222. In alternative embodiments, one circuit board 210 connects with elements 24 in different modules 222, or elements 24 in a same module 222 connect with different circuit boards 210. A seventh circuit board comprises a control logic circuit board. The control logic circuit board interfaces with the base unit 12 for operating the transmit and receive circuitry. The printed circuit boards 210 and other components of the probe 18 are sized to fit within the handle of the probe 18. The probe 18 is designed for ergonomic handling by a user, such as being less than four inches in diameter or providing a handheld grip.

In one embodiment, the circuit boards include one or more multiplexers. For example, a plurality of eight to one multiplexers are provided for multiplexing signals from the elements 24 onto 192 system channels or cables 22. In other embodiments, fewer or more multiplexers for use with fewer or more cables 22 or system channels are provided. For example, an array 200 of 64 rows 202 and 32 columns 204 is provided with multiplexers for transmitting time division multiplexed information on 256 cables 22. Providing the multiplexer in the probe 18 with the array 200, fewer cables 22 and associated system channels or signal lines are provided than the number of elements 24 of the array 200. For example, the product of the number of elements along the elevation dimension and the number of elements along the azimuth dimension is greater than the number of cables 22.

The circuit boards 210 connect with the flexible circuits 206 and 208 using any now-known or later developed connectors or connections. Using two or more separate signal traces for each element 24 provides electrical connections for twice the number of elements 24. The connectors are attached to the flexible circuits 206, 208 prior to array fabrication. In one embodiment, a ball grid array (BGA) or other matrix of bumps or other structures for soldering to the traces on the flexible circuits 206 and 208 are provided. Small pitch matrix type BGA connectors may be used. For example, the BGA connects the receive path signal traces to the multiplexer, and the multiplexer is then connected to the printed circuit boards, reducing the number of connections to the printed circuit boards. In another embodiment, transmit or receive circuitry are deposited or otherwise formed on the flexible circuit, resulting in the need for fewer connections from the flexible circuits 206, 208 to the printed circuit boards 210. In yet another embodiment, a direct attachment, such as wire bond jumping or other interconnections, is provided between the flexible circuit and the printed circuit boards.

Figures 11A, 11B:
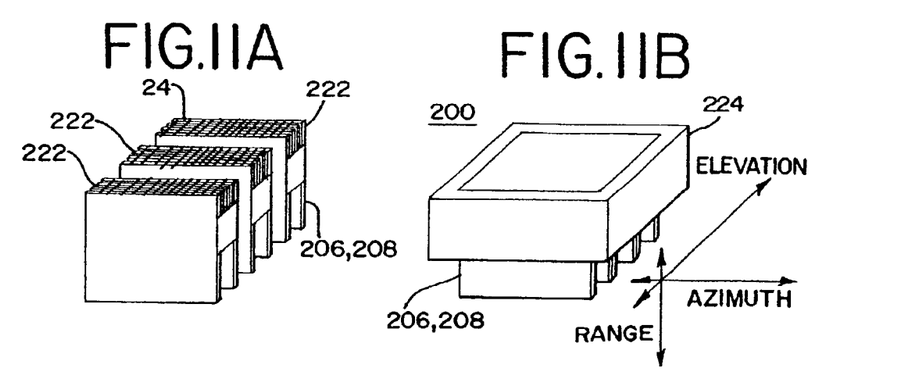
FIGS. 11A and 11B are graphical representations of steps performed for manufacturing a multi-dimensional array using pre-diced modules.

FIGS. 11A and B represent acts in a process for manufacturing the array 200. FIG. 11A shows three modules of elements 24. Each module 222 includes at least two rows and two columns of elements 24 in an N by M array. The PZT layer 214 of each module 222 and the associated flexible circuits 208, 206 are diced independently for each module 222. The dicing includes one or both of dicing along the azimuth or elevation dimensions to form the elements 24. By dicing the electrodes or flexible circuits 208, 206 separately for each module 222, each module 222 may be tested separately. Separate testing allows for disposal of a defective module 222 before final assembly. For example, capacitants tests or acoustic tests are performed for each element 24 of each of the modules 222.

Each of the separately diced modules 222 is formed as shown in FIG. 10. Any of various manufacturing processes may be used, and different orders of assembly provided. In one embodiment, the first matching layer 216, a slab of piezoelectric layer 214 and a flexible circuit 206 positioned on the bottom of the piezoelectric layer 214 are stacked on top of the backing layer 220. Precision tooling with pins and associated holes or templates are used for aligning these layers. The bottom flexible circuit 206 has signal traces on both sides for connecting with different elements 24. The aligned layers are then bonded or glued together.

After bonding, the bottom layer of flexible circuit material 206 is folded along the sides of the backing layer 220 below the layer of piezoelectric layer 214. The width of the backing layer 220 is narrower than the width of the piezoelectric layer 214 by about the width of one or two layers of the flexible circuit 206. In one embodiment, the flexible circuit 206 is folded on two sides of the backing layer 220, but may be folded on just one side. The bottom flexible circuit 206 is tightly bonded to the backing material by placing the partial module 222 through a Teflon coated or other frame with bonding material or glue. Alternatively, the bottom flexible circuit 206 is bonded to the sides of the module 222 during a later act of bonding the top flexible circuit 208.

The first matching layer 216 and piezoelectric layer 214 are diced along the azimuth dimension. For example, six major dicing kerfs are formed that extend into, but not through, the flexible circuit material 206. Minor dicing kerfs may also be formed along the azimuth dimension. The minor dicing kerfs extend about 90% into the piezoelectric layer 214. Other dicing depths may be used. Epoxy, silicone or other material is used to fill the diced kerfs. A kerf-filling material with a higher acoustic impedance may be used since only the piezoelectric layer 214 and the first matching layer 216 are diced in azimuth. In alternative embodiments, other layer are diced in azimuth and a lower acoustic impedance kerf-filling material is used. In alternative embodiments, no kerf-filling material is used.

The surface of the first matching layer 216 is ground or otherwise processed to remove any excess kerf-filling material if necessary. The top flexible circuit 208 and the second matching layer 218 are aligned and bonded together using pins and holes or templates. The bonded top flexible circuit 208 is then bonded to bottom matching layer 216. In alternative embodiments, the top flex 208 and top matching layer 218 are aligned and bonded to the bottom matching layer 216 on the module 222 as one operation associated with filling the kerfs.

The position of the top flex circuit 208 and associated signal traces relative to the bottom flex circuit 206 and associated signal traces is within a tolerance sufficient to allow separate signal traces for each element 24. For example, a tolerance of plus or minus 50 $\mu$m allows a dicing area of 100 $\mu$m between each of the elements 24 along the elevation dimension without adversely cutting a signal trace. Other tolerances and distances are possible. The alignment is performed using precision-tooled pins and holes, template or optical alignment. By providing signal traces on flex circuits 206, 208 on both sides of the module 222, less dense signal traces are provided, allowing larger dicing windows. In alternative embodiments, a greater density of signal traces is provided and the flexible circuits 208 and 206 are provided on one side of the module 222.

The top flexible circuit 208 is folded along one or two sides of the piezoelectric layer 214 and backing layer 220. The flexible circuit 208 extends from the piezoelectric layer 214 towards the backing material 220. Where signal traces are provided on a top side or outward facing side of the bottom flexible circuit 206 and on a bottom or inward facing side of the top flexible circuit 208, an insulation layer is added between the two flexible circuits 206 and 208. For example, a 25 $\mu$m or other thickness of Teflon or electrically non-conductive material is applied to one or both of the flexible circuit layers 206 prior to assembly or during assembly. The upper flexible circuit 208 is then bonded to the sides of the modules 222 by passing through a frame with a Teflon coating or other coating. Both flexible circuits and the associated electrodes are bonded to the module 222.

The module 222 is then diced in the elevation dimension, such as dicing to form 64 columns 204 of elements 24. The dicing extends through both flexible circuits 206 and 208 and the piezoelectric layer 214 into the backing layer 220. In one embodiment, no minor dicing kerfs are provided, but minor dicing kerfs may be used. In one embodiment, the top flexible circuit 208 is examined through a microscope for optically aligning the dicing saw. The elevational dices in combination with the earlier azimuthal dices define the elements 24. The elevational dices may be provided for each of the modules 222 at a same time or at different times. The dicing results in top and bottom separate electrodes and associated signal traces for each of the elements 24 without a grounding plane common to all of the elements. In alternative embodiments, a grounding plane is used with only one separate signal trace for each element 24.

The separately diced modules 222 are aligned as shown in FIG. 11B. The modules 222 are positioned adjacent to each other along the elevation or azimuth dimension to form a larger array 200 of elements 24. Each of the modules 222 is separated from another module 222 by one or more of the flexible circuits 206, 208. In one embodiment, each of the modules 222 represents 64 azimuthally-spaced rows 202 and four or six elevationally-spaced columns 204 of elements 24. By aligning four or six modules 222 in the elevation and azimuth dimensions, a 64 by 24 grid of elements 24 is provided. Other number of modules, sizes and number of elements grids may be used with or without separation of modules 222 by flexible circuits 206, 208.

The top flexible circuit 208 has signal traces formed on a bottom side so that the flexible circuit 208 electrically insulates the signal traces of one module 222 from the signal traces of another module 222. In alternative embodiments, an insulator material, such as additional Kapton or other material, is positioned between the two modules 200 for electrical isolation of the signal traces.

Prior to aligning, each of the modules 222 is pressed through a Teflon-covered frame or other frame with glue or other bonding material. The pressing tightly fits the flexible circuits 206 and 208 along the sides of the modules 222 for minimizing any separation between modules.

The modules 222 are positioned within a frame 224. The frame comprises a graphite material, another conductive material, or other non-conductive material. The four modules 222 either press-fit within the frame 224 or are positionable within the frame 224. When the modules 222 are positioned within the frame 224, the spacing between the PZT layer 214 of the modules 222 is 50–150 micrometers, but other spacing may be used. The spacing is the result of the flexible circuit material between the piezoelectric layers 214 of each module 222. A 50–150 micrometer spacing is either 0–100 micrometers larger than a normal kerf width. Other relative widths may be used. Minimizing the separation between modules 222 minimizes the beam width in the elevation dimension or the elevation point spread function. The frame 224 aligns the modules 222 in both dimensions but may provide less tolerance within an azimuth dimension. Higher tolerance alignment may be provided through manual optical alignment, pin and hole alignment or precise machining of the frame 224 as a template.

After the modules 222 are aligned within the frame 224, the kerfs from the separate dicing are filled with silicone or other kerf-filling material. The kerf-filling material also acts to bond the modules 222 to each other and the frame 224. In alternative embodiments, the kerfs of the modules 222 are filled prior to alignment. In alternative embodiments, no kerf filling is used. A protective layer of lens material or other focusing or non-focusing acoustically transparent material is positioned over or around the array 200. For example, high temperature or room temperature vulcanized silicon is formed over the array 208. Where the array 200 is fully sampled, the additional protective layer provides for no focus or limited focus.

The flexible circuits 206, 208 and associated signal traces are connected to the printed circuit boards or multiplexers. The output of the multiplexers are connected to cables 22. The cables electrically connect the elements 24 of the array 200 to the base unit 12.

In alternative embodiments, different multi-dimensional arrays are provided with a multiplexer integrated within the probe 18 and/or isolation of transmit and receive paths by the transducer element 24. Multiplexing allows multiplexing of multiple channels onto a single channel, such as through time division multiplexing. The amount of multiplexing, the bandwidth desired, the center frequency, and the clock rate determine the amount of multiplexing used. For example, a system with a 40 MHz clock rate may use up to a 25 MHz center frequency transducer assuming Nyquist sampling rate up to 1.6 times the center frequency. With multiplexing, the center frequency may be reduced to reduce the number of system channels or cables 22. In the example above, a 2:1 multiplexer allows use of up to a 12.5 MHz center frequency transducer with a 120% bandwidth, but doubles the number of elements 24 using one cable 22. A 3:1 multiplexer allows use of up to a 8.3 MHz center frequency transducer. 4:1 allows 6.3 MHz, 5:1 allows 5.0 MHz, 6:1 allows 4.2 MHz, 7:1 allows 3.6 MHz and 8:1 allows 2.5 MHz. Higher clock rates allow either more multiplexing or higher center frequency transducers.

Some multi-dimensional arrays provide a plurality of transducer elements arranged with N elements along a first dimension where N is greater than one and with M elements along a second dimension where M is greater than one and not equal to N. For example, a multi-PZT layer linear array, a 1.5D, I-beam, +-beam or other arrays of elements 24 have different distributions of elements 24. A probe houses the array 200 of elements 24. A multiplexer within the probe and connected to at least two of the plurality of transducer elements 24 allows for a greater number of elements 24 with a fewer number of system channels or cables 22 connected to the base unit 12.

Multiplexing allows higher resolution use of 1.5 dimensional transducer arrays, such as arrays with two or more elevation rows of 96 elements 24 in the azimuth dimension. For example, with 2:1 time domain multiplexing, a 1.5D array with three or four rows of 96 elements uses 192 system channels or cables 22 at up to 12.5 MHz. With 7:1 multiplexing of 7 segments or rows of 96 elements 24, the array may operate at up to 3.6 MHz with 192 system channels or cables 22 in a 40 MHz clock rate system.

A plano-concave transducer with isolated left and right elevation aperture spaced elements 24 may also benefit from multiplexing. For example, see the arrays described in U.S. Pat. No. 6,043,589, the disclosure of which is incorporated herein by reference. Two or three segmented arrays operate at a higher center frequency and/or with more elements by multiplexing signals from one or more elements with signals from another element.

Transducers configured as two or more separate or intersecting linear or curved linear arrays may also benefit from multiplexing. A first linear array is positioned along one dimension and a second linear array is positioned along the second dimension or not parallel to the first array. For example, the various I-beam, +-beam or other arrays disclosed in U.S. Pat. No. 6,014,473, the disclosure of which is incorporated herein by reference, use multiplexing to allow for a greater number of elements with the same or fewer cables 22. In this example, one linear array is used for imaging and one or more other orthogonal arrays provide tracking information. By multiplexing, image resolution is sacrificed less by using system channels or cables for tracking arrays. For example, one imaging and two tracking arrays each use 192 elements 24 with 3:1 multiplexing to 192 cables 22. Other distributions of elements 24 within the arrays may be used.

Bi-layer or multiple layer transducer arrays may also benefit from multiplexing. Two or more layers of PZT within a linear or other array of elements 24 are used for harmonic imaging. One or more one dimensional arrays of elements 24 along the azimuth dimension have layers of elements 24 or PZT along the range dimension. For example, the arrays disclosed in U.S. Pat. No. 6,673,016 (Ser. No. 10/076,688, filed Feb. 14, 2002) or U.S. Pat. No. 5,957,851 use multiple layers of elements 24 separated by electrodes. Multiplexing allows for a greater number of separately addressable PZT layers and/or elements 24. The relative phasing of one layer to another layer provides for either fundamental or harmonic operations.

A square grid of elements as a two-dimensional array or a single linear array may also benefit from multiplexing. Multiplexing allows for more elements with fewer system channels or cables 22. Multiplexing provides higher resolution and/or faster scanning for two or three dimensional imaging.

While the invention has been described above by reference to various embodiments, it should be understood that many changes and modifications can be made without departing from the scope of the invention. It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. An ultrasound transmit pulser system with receive interconnection, the system comprising:

a transducer element;

a DC power source;

an amplifier;

a first switch connected with the transducer element and a first input of the amplifier; and     a second switch connected with the transducer element and the DC power source.

2. The system of claim 1 wherein the first and second switches connect with a same electrode of the transducer element.

3. The system of claim 1 wherein the transducer element and first and second switches are positioned in a probe, and further comprising:

a cable connectable between the probe and a base unit.

4. The system of claim 1 wherein the transducer element and amplifier are positioned in a probe, and further comprising:

a cable connectable between the probe and a base unit.

5. The system of claim 4 further comprising a multiplexer connected with an output of the amplifier and the cable, the multiplexer positioned in the probe, the probe separate from the base unit.

6. An ultrasound transmit pulser system with receive interconnection, the system comprising:
a transducer element;
a power source;
an amplifier;
a first switch connected with the transducer element and a first input of the amplifier; and
a second switch connected with the transducer element and the power source;
wherein at least two diodes electrically connect with the first switch and the first input of the amplifier, the two diodes comprising a diode clamp.

7. The system of claim 1 further comprising:
a third switch connected with the transducer element and a second input of the amplifier; and
a fourth switch connected with the transducer element and the power source.

8. The system of claim 7 wherein the first, second, third and fourth switches comprise a H bridge of transistors around the transducer element, the first and second switches connecting with a first electrode of the transducer element and the third and fourth switches connecting with a second electrode of the transducer element, the second electrode different than the first electrode.

9. The system of claim 8 further comprising first and second diode clamps connected with the first and second inputs, respectively, of the amplifier, the amplifier comprising a differential amplifier.

10. The system of claim 8 wherein the first and third switches conduct and the second and fourth switches are nonconductive to provide a substantially zero voltage to the transducer element, the first and fourth switches conduct and the second and third switches are nonconductive to provide a positive voltage to the transducer element, and the second and third switches conduct and the first and fourth switches are nonconductive to provide a negative voltage to the transducer element.

11. An ultrasound transmit pulser system with receive interconnection, the system comprising:
a transducer element;
a power source;
an amplifier;
a first switch connected with the transducer element and a first input of the amplifier; and
a second switch connected with the transducer element and the vower source;
wherein the first switch conducts and the second switch is nonconductive during receive operation, and the first and second switches alternate between conductive and nonconductive states during transmit operation.

12. The system of claim 1 wherein the system is free of any switch operable to select between a transmit path and a receive path.

13. The system of claim 1 wherein all electrodes of the transducer element are free of a direct connection to ground.

14. The system of claim 1 wherein the amplifier comprises a low voltage amplifier.

15. The system of claim 9 wherein the first and second switches comprise high voltage switches in a first application specific integrated circuit and the first and second diode clamps and amplifier comprises low voltage devices in the first application specific integrated circuit.

16. The system of claim 7 wherein the first and third switches comprise first matched switches and the second and fourth switches comprise second matched switches.

17. A method for using an ultrasound transmit pulser system with receive interconnection, the method comprising:
(a) switchably connecting a transducer element to a first input of an amplifier with a first switch; and
(b) switchably connecting a power source to the transducer element with a second switch;
(c) alternately performing (a) and (b) during a transmit operation; and
(d) disconnecting the power source with the second switch and connecting the transducer element to the first input with the first switch during receive operation.

18. The method of claim 17 further comprising:
(e) limiting a voltage at the transducer element during (a) and (d) with a diode clamp.

19. The method of claim 17 wherein (a) and (b) are operable to connect with a first electrode of the transducer element;
further comprising:
(e) switchably connecting the transducer element to a second input of the amplifier with a third switch, the second electrode different than the first electrode; and
(f) switchably connecting the power source to the second electrode of the transducer element with a fourth switch; and
(g) alternately performing (e) and (f) during the transmit operation;
wherein (d) comprises (i) disconnecting the power source with the second and fourth switches and (ii) connecting the first electrode to the first input with the first switch and connecting the second electrode to the second input with the third switch during receive operation.

20. An ultrasound transmit pulser system with receive interconnection, the system comprising:
a transducer element having first and second electrodes on opposite sides of transducer material;
an H-bridge of transistors, first and second transistors of the H-bridge connected with the first electrode and third and fourth transistors of the H-bridge connected with the second electrode;
a differential receive amplifier connected with the first and third transistors; and
first and second diode clamps connected with the first and third transistors, respectively.

21. The system of claim 1 wherein the first and second switches connect with a first electrode of the transducer element and a second electrode of the transducer element is connected to a ground.

22. An ultrasound system for medical diagnostic imaging, the system comprising:
a transducer having at least one element;
a receive beamformer comprising an amplifier, the receive beamformer connected with the transducer;
a transmit beamformer comprising a power source, a first switch connected with the at least one transducer element and a first input of the amplifier and a second switch connected with the at least one transducer element and the power source, wherein the first switch conducts and the second switch is nonconductive during receive operation and the first and second switches alternate between conductive and nonconductive states during transmit operation; and
an image processor connected with the receive beamformer.

* * * * *